(12) United States Patent
Frank et al.

(10) Patent No.: US 9,834,508 B2
(45) Date of Patent: Dec. 5, 2017

(54) METHOD FOR SEPARATING ISOCYANATE MONOMERS

(71) Applicant: Rathor AG, Appenzell (CH)

(72) Inventors: Brian Frank, St. Gallen (CH); Christoph Kellenberger, Zurich (CH)

(73) Assignee: Rathor AG, Appenzell (CH)

( * ) Notice: Subject to any disclaimer, the term of this patent is extended or adjusted under 35 U.S.C. 154(b) by 0 days.

(21) Appl. No.: 15/103,207

(22) PCT Filed: Dec. 18, 2014

(86) PCT No.: PCT/EP2014/078479
§ 371 (c)(1),
(2) Date: Jun. 9, 2016

(87) PCT Pub. No.: WO2015/091807
PCT Pub. Date: Jun. 25, 2015

(65) Prior Publication Data
US 2016/0304444 A1     Oct. 20, 2016

(30) Foreign Application Priority Data

Dec. 18, 2013 (DE) .................. 10 2013 021 060

(51) Int. Cl.
*C07C 263/20* (2006.01)
*C08G 18/10* (2006.01)
(Continued)

(52) U.S. Cl.
CPC .......... *C07C 263/20* (2013.01); *B01D 61/243* (2013.01); *B01D 69/02* (2013.01);
(Continued)

(58) Field of Classification Search
None
See application file for complete search history.

(56) References Cited

U.S. PATENT DOCUMENTS 2,988,538 A * 6/1961 Thoma ............... C08G 18/0804
528/44
3,415,790 A * 12/1968 Davis ..................... C08G 18/10
264/184
(Continued)

FOREIGN PATENT DOCUMENTS

| EP | 2042485 A1 | 1/2009 |
| EP | 2298435 A1 | 3/2011 |
| WO | WO 2012/097967 | * 7/2012 |

OTHER PUBLICATIONS

Strathmann ("Membranes and Membrane Separation Processes, 1. Principles (DOI: 10.1002/14356007.a16_187.pub3) and 2. Design and Operation (DOI: 10.1002/14356007.o16_o03)" Ullmann's Encyclopedia of Industrial Chemistry, published online Nov. 15, 2011, p. 413-481).*

(Continued)

*Primary Examiner* — Jafar Parsa
*Assistant Examiner* — Amy C Bonaparte
(74) *Attorney, Agent, or Firm* — Berliner & Associates

(57) ABSTRACT

The invention relates to a method for the separation of isocyanate monomers from isocyanate-containing mixtures by the provision of the mixture in a solvent and dialysis of the dissolved mixture against the solvent by means of a permeable membrane having a pore size in the range of between 5 and 400 nm. The method may in particular be employed for the separation of isocyanate monomers from prepolymers containing isocyanate groups, with said prepolymers being used for the production of adhesives, insulating, and expanding foams.

11 Claims, 1 Drawing Sheet

(51) Int. Cl.
*B01D 69/02* (2006.01)
*B01D 71/52* (2006.01)
*B01D 61/24* (2006.01)
*B01D 71/48* (2006.01)
*B01D 71/50* (2006.01)
*B01D 71/54* (2006.01)
*B01D 71/68* (2006.01)
*B01D 71/70* (2006.01)
*B01D 71/28* (2006.01)
*B01D 71/40* (2006.01)

(52) U.S. Cl.
CPC ............. *B01D 71/48* (2013.01); *B01D 71/50* (2013.01); *B01D 71/52* (2013.01); *B01D 71/54* (2013.01); *B01D 71/68* (2013.01); *B01D 71/70* (2013.01); *C08G 18/10* (2013.01); *B01D 71/28* (2013.01); *B01D 71/40* (2013.01); *B01D 2315/14* (2013.01); *B01D 2325/02* (2013.01); *B01D 2325/04* (2013.01)

(56) References Cited

U.S. PATENT DOCUMENTS

| | | | |
|---|---|---|---|
| 2004/0109888 A1* | 6/2004 | Pun | A61K 9/0014 424/450 |
| 2007/0014755 A1* | 1/2007 | Beckman | A61K 31/28 424/78.27 |
| 2010/0213126 A1* | 8/2010 | Carr | B01D 61/027 210/638 |
| 2016/0022872 A1* | 1/2016 | Wells | A61L 27/18 424/400 |
| 2016/0184437 A1* | 6/2016 | Chen | C08G 18/6212 514/20.3 |

OTHER PUBLICATIONS

English language machine generated translation of EP 2298435, p. 1-13, Feb. 23, 2011.*

* cited by examiner

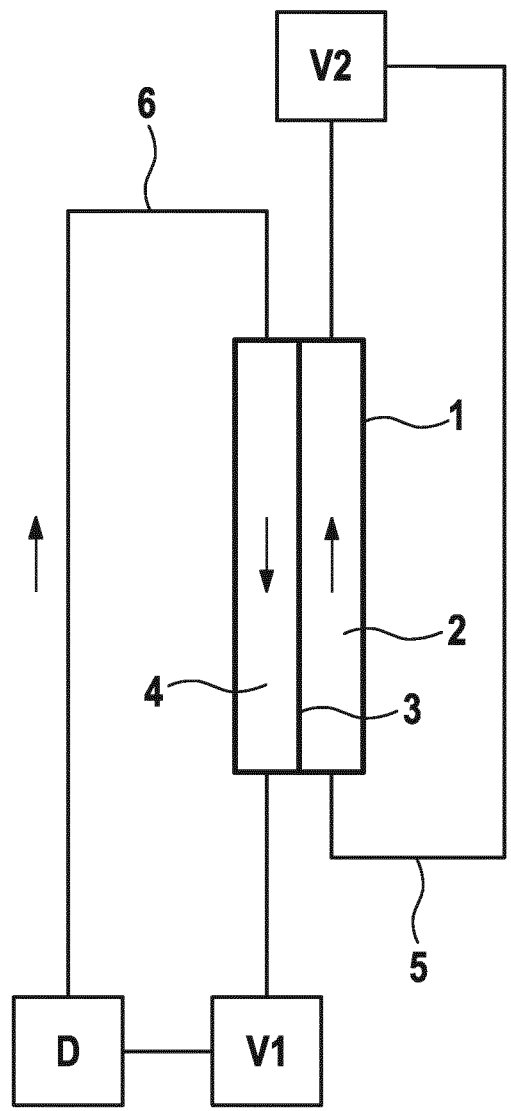

METHOD FOR SEPARATING ISOCYANATE MONOMERS

The invention relates to a method for the separation of isocyanate monomers from mixtures containing monomeric isocyanates.

Isocyanate-containing prepolymers play a significant role in the production of expanding and insulating foam materials discharged from aerosol cans with a view to foam mounting, for example, door and window casings in buildings or closing off openings in brickwork. Further application examples of such prepolymers is the making of adhesives, in particular of spray adhesives or glues.

Such isocyanate-containing prepolymers are usually produced by crosslinking of diphenylmethane diisocyanate (MDI), its polynuclear analogs, toluylene diisocyanate (TDI), and hexamethylene diisoyanate (HDI) with polyols and/or polyesterols. Quite a number of other isocyanates are known that may be used for a crosslinking reaction with polyols or polyesterols.

Prepolymers produced in this manner usually contain monomeric isocyanates to a greater or lesser extent. These monomeric isocyanates are volatile to a certain degree and respirable when in aerosol form. Furthermore, they are also toxic. For that reason, the content of monomeric isocyanates in such prepolymers is subject to legal restrictions.

The content of monomeric isocyanates in prepolymers of this nature may, on the one hand, be limited by adopting a conducive reaction regime during production and by selecting customary basic substances. However, these measures are highly sophisticated and will make the product more expensive.

A number of isocyanate monomers can also be removed by taking distillative measures. Used in this context are, for example, the thin film distillation, also in the presence of an entraining agent, for instance a high-boiling phosphoric acid ester (TMCP). Such phosphoric acid esters may to a certain extent be retained within the monomer-depleted prepolymers because they serve flame-retarding purposes.

Distillative methods of this kind are to be realized relatively easily, however they will also cause significant thermal stresses to act on the product resulting in changes with respect to its crosslinking characteristics and viscosity. This imposes, however, limitations on the formulation of the finished prepolymer mixtures used for the aerosol cans. Measures must be taken with respect to ensuring the solubility of the prepolymer in the propellant mixture used for the aerosol can and appropriately adjust the viscosity to an acceptable value.

Bearing all this in mind, new methods are needed for the depletion of monomers from isocyanate-containing prepolymers, said methods not being subject to the restrictions described hereinbefore, especially do not result in thermal stresses to act on the prepolymer.

This objective is accomplished by providing a method that enables the mixture to be provided in a solvent, said dissolved mixture than being dialyzed against the solvent by using a permeable membrane having a pore size ranging between 5 and 400 nm. Said mixtures consist in particular of prepolymers containing isocyanate monomers employed for the production of expanding, adhesive, and insulating foams to be discharged from aerosol cans.

The method proposed by the invention is based on the separation of low-molecular constituents from isocyanate-containing prepolymers with the help of permeable membranes. Such low-molecular constituents are mainly the monomers from which the prepolymers are produced making use of crosslinking components, said monomers essentially being MDI, TDI, and HDI; however, the method can also be applied to other monomers containing isocyanate groups, for example isophorone diisocyanate (IPDI) or dicyclohexylmethane or diisocyanate (H12MDI).

In particular, the method can also employed for the separation of MDI monomers from crude MDI, a mixture of MDI and homologous aromatic isocyanates.

To enable the dialytic separation of the monomers from the prepolymers to be achieved the prepolymer has to be dissolved in a solvent. For this purpose, polar solvents or mixtures containing polar solvents can basically be employed. Suitable solvents are in particular ethers and esters, however ketones and halogenated solvents may also be used.

Among the esters, the lower alkyl esters of formic acid and acetic acid are to be mentioned here, for example the methyl and ethyl esters. Suitable as well are phosphoric acid esters, for example tris(monochloropropyl) phosphate (TMCP), the complete and thorough separation of which from the depleted prepolymer can often be dispensed with as TMCP may be employed in adhesive, expanding, and insulating foams for the purpose of flame retardation. Moreover, also to be mentioned are ethers, for example dioxolane, THF, dimethyl ether, and diethyl ether, but also methylal. Another suitable ether would be methyl tertiary-butyl ether. Among the ketones, also usable for the purpose is acetone.

Dichloromethane can be employed as halogenated solvent, for example.

Generally speaking, solvents are preferred that aside from efficient solvent characteristics also have a low boiling point so as to enable separation to be easily achieved. In the event dimethyl ether is used the process has to be carried out under pressure due to the low boiling point. In this case as well the ether may (partially) remain in the depleted prepolymer and be used in the aerosol can as propellant.

The prepolymer dissolved in the solvent or solvent mixture is dialyzed through a permeable membrane. To enable the necessary permeability to be achieved the membrane has a pore size ranging between 5 and 400 nm, preferably is in the range of between 15 and 200 nm, and in particular between 25 and 100 nm. It is of course clear that said membrane is of open-pored design so as to warrant the required permeability during the dialysis.

In general, the membrane has a thickness of between 0.05 and 50 μm, preferably ranging between 0.5 and 40 μm, and especially preferred between 5 and 20 μm. The thickness of the membrane is usually selected with a view to achieving the necessary stability as well as maximum permeability for the relevant monomer. Due to the fact that the membrane is impermeable for the higher molecular constituents of the mixture it may also be regarded as a semi-permeable membrane.

The membrane consists of customer plastic materials the porosity of which being provided in a manner known per se. Plastic materials especially suited are polysulfones, polyether sulfones, polycarbonates, polyethers, polyesters, polyacrylates, polysiloxanes, polystyrene as well as copolymers thereof. Preferred are polysulfones, polyether sulfones, and polyether ether ketones.

Regarding the production of membranes of suitable porosity reference is made to publication WO 2012/097967 A1. In that publication a method has been described that provides for a plastic material to be dissolved in a solvent, with the respective solution being mixed with a dispersion of nanoparticles of a suitable salt, for instance calcium carbonate, sodium carbonate or sodium chloride. The pore size of the permeable membrane is governed by the size of the salt particles. After homogenization the dispersion/solution is applied to a substrate in the desired thickness. The salt particles are washed out of the film with the help of an acid (calcium carbonate), respectively water (soluble salts). Following this, the film is washed using water and ethanol, dried, and then removed from the substrate material.

Several variants of this production method with different techniques have been described in detail in publication WO 2012/097967 A1. As regards the membranes and their production express reference is made to this publication.

The method proposed by the invention can be carried out at normal pressure but also at elevated pressure, for instance to enhance dialysis or be able to make use of low-boiling solvents or solvent mixtures as well.

Dialysis is performed using the same solvent in which the prepolymer has been dissolved. Preferred is a countercurrent method wherein the monomer-rich prepolymer solution flows countercurrently to fresh monomer-free solvent on the other side of the dialysis membrane. Normally, contact times of between 0.1 and 4.0 h are considered sufficient. Good results are achieved with contact times between 0.5 and 1 h.

The inventive method enables depletion values to be achieved that are in the range of the limit of detection.

Obviously, the solvent must then be eliminated at least partially from the monomer-depleted prepolymer. This is achieved by simple distillation which in case of low-boiling solvents makes it possible to keep the thermal stresses acting on the prepolymer to a minimum. If thought expedient, distillation may take place under vacuum. In the event of DME being used as solvent said solvent can to a great extent by removed again and recovered by simply bringing the pressure down to normal.

The invention is explained in more detail by way of the following examples.

EXAMPLE 1

With a dialysis volume of 2 ml an MDI-containing prepolymer, dissolved in TMCP at a ratio of 1:20, was dialyzed against 1000 ml of TMCP. For dialysis, a polyethersulfone membrane having a pore size of 55 nm was used. The thickness of the membrane was 20 µm.

The source material contained 5.8% w/w of monomeric MDI.

After a dialysis duration of half an hour the content of monomeric MDI was found to be below the detection limit.

EXAMPLE 2

A solution of a prepolymer with a content of 13.2% w/w of monomeric MDI in TMCP at a ratio of 1:20, dialysis volume 2 ml, was dialyzed against 200 ml of TMCP. After a dialysis time of ten minutes the sample content of MDI was 7.4%, after thirty minutes of dialysis it was found to be 2.9%.

Comparable results were achieved with acetone, THF, and ethyl acetate being used as solvent.

EXAMPLE 3

FIG. 1 shows a schematic representation of a dialysis apparatus to be used in accordance with the invention. In a dialysis vessel 1 the dissolved mixture (channel 2) and the solvent (channel 4) are run countercurrently in channels 2 and 4 separated by a permeable membrane 3. Passing through membrane 3 the isocyanate monomers in channel 2 and are entering the solvent present in channel 4 from where they are evacuated.

The representation shows a discontinuous process configuration wherein the mixture is circulated (channel 2, line 5) and collected in collecting vessel V2.

Depletion of the monomer takes place in several cycles through membrane 3. Countercurrently, the solvent is run through line 6 and channel 4. The monomer-laden solvent accumulates in collecting vessel V1. The solvent is separated from the monomer solution by distillation (distillation/condensation D) and added again to the solvent stream. The monomer accumulates in vessel V1.

If the dialysis capacity is adequate, the method may also be carried out continuously. In this case, a single pass through the dialysis apparatus is sufficient. The separating efficiency of the apparatus is especially governed by the membrane surface, the flow velocity of the media, and the ratio between membrane surface and existing volume of the medium.

The invention claimed is:

1. A method for separating an isocyanate monomer from a mixture comprising an isocyanate-containing prepolymer and the isocyanate monomer, the method comprising
dissolving the mixture in acetone as a solvent, and subjecting the dissolved mixture to dialysis against acetone with a permeable membrane made from polyetheretherketone,
wherein the membrane has a pore size in the range of between 5 and 400 nm.

2. The method according to claim 1, wherein the membrane has a pore size ranging between 15 and 200 nm.

3. The method according to claim 1, wherein the membrane has a thickness of between 0.05 and 50 µm.

4. The method according to claim 1, wherein said method is used for the separation of monomeric diphenylmethane diisocyanate (MDI), toluylene diisocyanate (TDI) or hexamethylene diisoyanate (HDI) from prepolymers.

5. The method according to claim 1, wherein the dialysis takes place in a dialysis vessel, wherein the dialysis vessel is divided by the permeable membrane, wherein one side of the membrane comprises the dissolved mixture and the other side of the membrane comprises acetone and separated monomer, and wherein during dialysis the dissolved mixture is flowed in a direction countercurrent to that of the flow of the acetone and separated monomer.

6. The method according to claim 1, wherein the concentration of the mixture in the solvent is in the range of between 2 and 20% w/w.

7. The method according to claim 6, wherein the concentration of the mixture in the solvent is in the range of between 4 and 10% w/w.

8. The method according to claim 1, wherein the dialysis is carried out between 0.1 and 4.0 h.

9. The method of claim 2, wherein the pore size is in the range of between 25 and 100 nm.

10. The method of claim 3, wherein the membrane thickness is between 0.5 and 40 µm.

11. The method of claim 3, wherein the membrane thickness is between 5 and 20 µm.

* * * * *